United States Patent [19]
Lee et al.

[11] Patent Number: 5,948,627
[45] Date of Patent: Sep. 7, 1999

[54] IMMUNOBEAD FLOW CYTOMETRIC DETECTION OF ANTI-HLA PANEL-REACTIVE ANTIBODY

[75] Inventors: Jar-How Lee, Los Angeles; Rui Pei, Woodland Hills, both of Calif.

[73] Assignee: One Lambda, Canoga Park

[21] Appl. No.: 08/866,535

[22] Filed: May 30, 1997

[51] Int. Cl.$^6$ .................................................. G01N 33/53
[52] U.S. Cl. .................... 435/7.24; 435/7.1; 436/507; 436/518; 436/523; 436/533
[58] Field of Search .................... 435/7.1, 7.24; 436/518, 507, 533, 523, 800, 811

[56] References Cited

U.S. PATENT DOCUMENTS

| | | | |
|---|---|---|---|
| 4,918,000 | 4/1990 | Schubert | 435/7.1 |
| 5,223,397 | 6/1993 | Pouletty et al. | |
| 5,514,557 | 5/1996 | Moghaddam | 435/7.24 |
| 5,567,627 | 10/1996 | Lehnen | 436/518 |

OTHER PUBLICATIONS

A. Nanni–Costa et al., "ELISA anti–HLA antibody screening identifies non–complement–fixing antibodies responsible for acute graft rejection. A case report." EUROPEAN JOURNAL OF IMMUNOGENETICS, 23(5):383–387, Oct. 1996.

A. Zachary et al., "Evaluation of HLA antibodies with the PRA–STAT test." TRANSPLANTATION, 60(12):1600–1606, Dec. 1995.

ATCC Catalogue of Cell Lines & Hybridomas, 7th edition, pp. 264, 323–324, 521, 1992.

Harmer et al., "Detectionof HLA Class I–and Clas 5 II–Specific Antibodies by Flow Cytometry and PRA–Stat Screening in Renal Transplant Patients," TRANSPLANTATION, 63(12):1828–1832, Jun. 1997.

Kao et al., "Enzyme–Linked Immunoassay for Anti–HLA Antibodies —An Alternative to Panel Studies by Lymphocytoxicity", TRANSPLANTATION, 55(1):192–196, Jan. 1993.

Kohler et al., "Flow cytometric detection of platelet–reactive antibodies and application in platelet crossmatching", TRANSFUSION, 36(3):250–255, Mar. 1996.

Massad et al., "Factors Influencing HLA Sensitization in Implantable LVAD Recipients", ANNALS OF THORACIC SURGERY, 64:1120–1125, Oct. 1997.

Parham, P., "Purification of Immunologically Active HLA–A and –B Antigens by a Series of Monoclonal Antibody Columns", THE JOURNAL OF BIOLOGICAL CHEMISTRY, 254(18):8709–8712, Sep. 1979.

Walker et al., "Human Histocompatibility Antigens: Isolation and Chemical Characterization", JOURNAL OF IMMUNOLOGICAL METHODS, 49:R25–R50, 1982.

Cantarero et al., *Anal. Biochem.*105: 375–382 (1980).
Frengen et al., *Clin. Chem.*40/3: 420–425 (1994).
Henderson et al., *Virology*76: 152–163 (1977).
Scillian et al., *Blood*73: 2041–2048 (1989).
Shroyer et al., *Transplantation*59: 626–630 (1995).
Sumitran–Karuppan et al., *Transplantation*61: 1539–1545 (1996).
Wilson et al., *J. Immunol. Methods*107: 231–237 (1988).
Zaer et al., *Transplantation*63: 48–51 (1997).

*Primary Examiner*—Carol A. Spiegel
*Attorney, Agent, or Firm*—Marshall, O'Toole, Gerstein, Murray & Borun

[57] ABSTRACT

The present invention provides an improved method for detection of panel reactive antibodies in serum of a subject against HLA class I antigens, which comprises the steps of adding serum from a subject to an array of microbeads, each microbead presenting HLA antigens from a cell population presenting the same HLA antigens; incubating the serum and microbeads for sufficient time for anti-HLA antibodies in the serum to bind to the HLA antigens presented on the microbeads; removing the serum components which do not specifically bind with the HLA antigens presented on the microbeads; incubating the microbeads with a labeled ligand capable of specifically binding with anti-HLA antibodies bound to said HLA antigens; removing the labeled ligand which is not bound to said HLA antigens; and detecting the presence of labeled ligand bound to said HLA antigens by flow cytometry.

15 Claims, 2 Drawing Sheets

# IMMUNOBEAD FLOW CYTOMETRIC DETECTION OF ANTI-HLA PANEL-REACTIVE ANTIBODY

BACKGROUND OF THE INVENTION

The present invention relates to methods for detection of anti-human leukocyte antigen (HLA) reactive antibodies. Individuals may be sensitized to HLA antigens during pregnancy, or by blood transfusion or previous organ grafts. Testing to determine sensitivity to HLA alleles is relevant to tissue and organ transplantation where the presence in the recipient of antibodies against HLA antigens of the donor (donor specific crossmatch) is predictive of a high risk of graft rejection. It is a standard practice in the transplant field to test all potential recipients against a panel of HLA antigens selected to represent a human population and the percentage of HLA alleles against which the serum is reactive is determined. In this panel reactive antibody (PRA) testing reaction of a patient's serum against a high percentage of HLA alleles present in a normal human population is predictive of a high risk of graft rejection.

Methods known in the art for HLA testing include the complement-dependent lymphocytotoxicity (CDC) test in which serum from a recipient is incubated with donor or panel lymphocytes followed by incubation with complement. The level of cytotoxicity is then estimated by discriminating between dead and viable cells using a dye. This method is labor intensive, requires viable cells, may be nonspecific and requires a subjective evaluation.

Pouletty et al. U.S. Pat. No. 5,223,397 discloses methods for testing HLA compatibility between a donor and a recipient comprising the steps of adding blood from the donor to a substrate having anti-HLA antibodies bound thereto and incubating for sufficient time for soluble HLA antigens present in the blood to bind to the antibodies or ligand. Blood from the recipient is then added to the solid substrate whereby any antibody specific for any HLA antigens bound to the solid substrate may become bound. The detection of an absence of antibodies from the recipient's blood to the HLA antigen is indicative of a cross-match.

Zaer et al., *Transplantation* 63: 48–51 (1997) discloses use of an ELISA using HLA class I molecules purified from pooled platelets to detect anti-HLA antibodies. The reference reports that in patients found to be unsensitized, the incidence of false-positive results was less for ELISA testing than for panel studies. In patients who were highly sensitized, both tests performed equally well, whereas discordant results were registered mainly in cases of mild sensitization. In such cases, the incidence of false-negative results was higher for ELISA testing than for panel studies.

Of interest to the present invention are assay methods making use of flow cytometry. Wilson et al., *J. Immunol. Methods* 107: 231–237 (1988) disclose the use of polyacrylamide microspheres coupled with cell membrane proteins in immunofluorescence assays for antibodies to membrane-associated antigens. The method is said to make possible the rapid flow cytometric analysis of plasma membrane antigens from cell populations that would otherwise be unsuitable for use in flow cytometry. Scillian et al., *Blood* 73: 2041–2048 (1989) disclose the use of immunoreactive beads in flow cytometric assays for detection of antibodies to HIV. Frengen et al., *Clin. Chem.* 40/3: 420–425 (1994) disclose the use of flow cytometry for particle-based immunoassays of α-fetoprotein (AFP). This reference further reports the ability of serum factors to cross-link labeled mouse monoclonal antibodies of irrelevant specificity to different particle types coated with various immunoglobulins.

Flow cytometry methods using lymphocytes are also known but suffer with difficulties because of the activity of auto-antibodies. See Shroyer et al., *Transplantation* 59:626–630. Moreover, when using flow cytometry with lymphocytes, use of ten or more different lymphocytes tends to result in confusing signals. As a consequence, studies using lymphocytes have been limited by presenting a small panel of HLA antigens that do not effectively simulate the distribution of HLA antigens in a normal human population.

Sumitran-Karuppan et al., *Transplantation* 61: 1539–1545 (1996) discloses the use of magnetic beads which use an anti-HLA capture antibody to immobilize a variety of soluble HLA antigens pooled from 80 to 100 individuals on each bead. The beads can then be directly added to patient serum for efficient absorption of HLA antibodies. The reference discloses visualization of antibody binding to the antigen-coated beads using flow cytometry. The reference suggests that this development will allow testing for antibody specificity for crossmatching purposes and for the screening of panel-reactive antibodies. The methods of Sumitran-Karuppan are limited, however, because the pooling of antigens causes sensitivity to certain rare HLA antigens. Moreover, the method is not capable of detecting the percentage of PRA.

Accordingly, there remains a need in the art for improved methods of HLA typing including methods for determination of percentage of PRA which is rapid, convenient and accurate.

SUMMARY OF THE INVENTION

The present invention generally relates to methods for detection of panel reactive antibodies in serum of a subject against HLA antigens including Class I and class II antigens. Specifically, the method comprises the steps of providing a collection of microbeads of different subtypes wherein microbeads of at least one subtype each present HLA antigens derived from a cell population presenting the same HLA antigens which is preferably but not necessarily a single lymphocyte cell line; adding serum from a subject to said collection of microbeads; incubating said serum and microbeads for sufficient time for anti-HLA antibodies in said serum to bind to said HLA antigens; removing said serum components which do not specifically bind with said HLA antigens presented on said microbeads; incubating said microbeads with a labeled ligand capable of binding with anti-HLA antibodies bound to said HLA antigens; removing said labeled ligand which is not bound to said anti-HLA antibodies; and detecting the presence of labeled ligand bound to said anti-HLA antibodies by flow cytometry. According to a preferred aspect of the invention, microbeads of each subtype present HLA antigens derived from a cell population presenting the same HLA antigens which can be derived from a single human individual and may be lymphocytes, platelets or another cell population which present HLA antigens. A preferred source is a single lymphocyte cell line. According to preferred methods of the invention, the panel of HLA antigens is selected to simulate distribution of Class I and/or Class II HLA antigens in a normal human population and also allows most rare antigens to be represented. According to particularly preferred methods, the panel comprises 54 different Class I HLA antigens obtained from 30 different cell lines. Alternatively, the panel can preferably comprise 22 different Class II HLA antigens preferably selected from 15 to 30 different cell lines. While the use of greater numbers of cell lines as sources for antigens can more closely simulate the natural distribution of antigens there is also a desire to minimize the number of cell lines used to promote greater sensitivity of the assay. Nevertheless, it will be within skill in the art to balance these factors in specifically designing an assay format.

The microbeads of the invention may be made of a wide variety of suitable materials with latex beads such as those available from Spherotech Inc. being particularly preferred. The microbeads may be of any size suitable for analysis by flow cytometry with diameters ranging from about 2 μm to about 15 μm being preferred and particles with diameters of about 3 μm being particularly preferred for beads presenting Class I HLA antigens and diameters of about 5 μm being preferred form beads presenting Class II HLA antigens. The invention further provides methods wherein microbeads of at least one HLA subtype differ from microbeads of at least one other HLA subtype by being selected to have different diameters or by having different labels such as are known to the art with fluorescent labels being preferred.

DETAILED DESCRIPTION OF THE INVENTION

Figure 1:
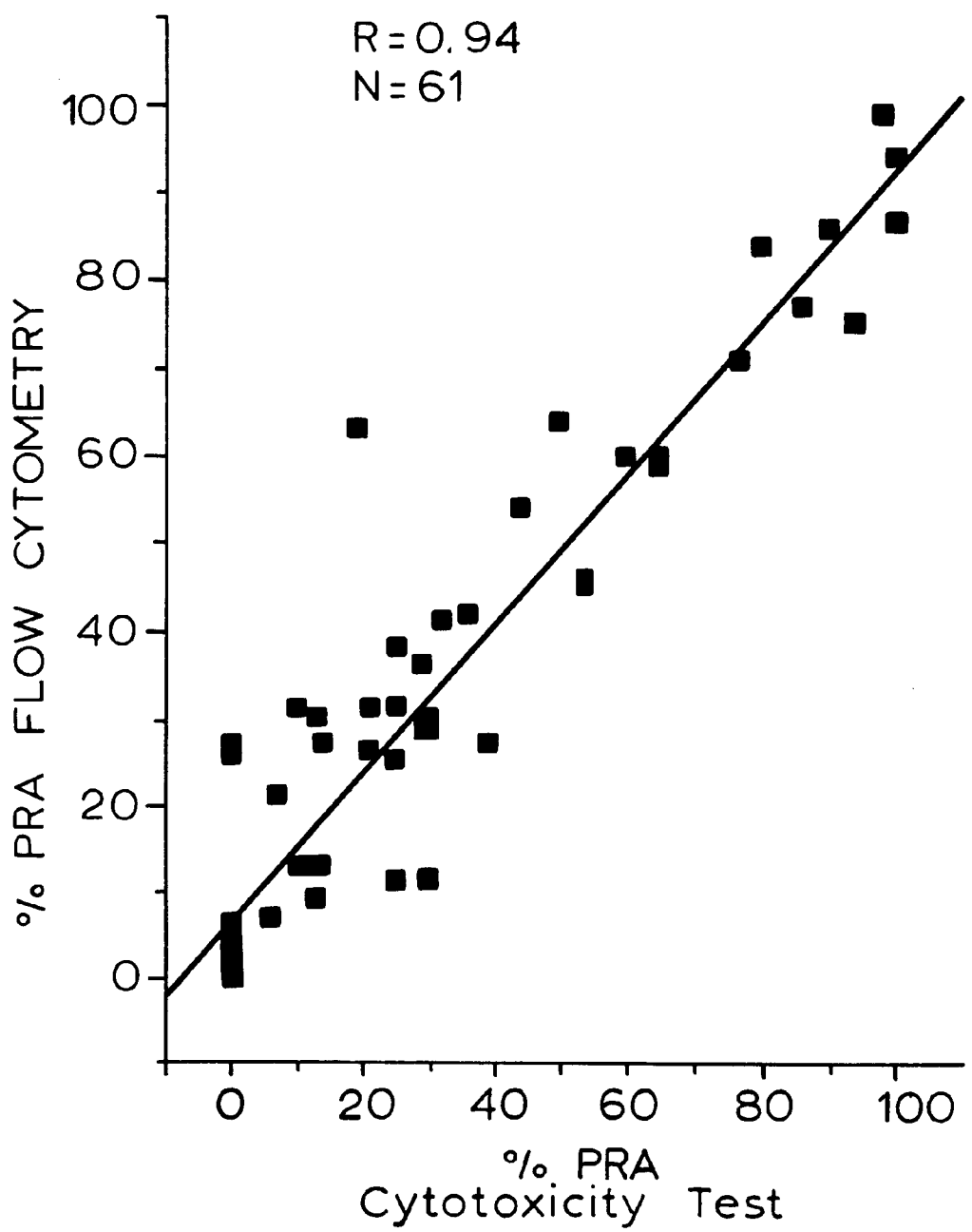
FIG. 1 depicts the correlation between the results of the method of the invention in determining the percentage PRA versus a standard cytotoxity test for sample sera.

The methods of the invention utilize microparticles coated with purified HLA antigen for detecting anti-HLA antibodies in human serum by flow cytometry. According to the methods of the invention, a panel of mixed microbeads coated with a panel of purified HLA antigens is used to detect percentage of PRA. The invention also provides an array of microbeads coated with different purified HLA antigens which are detectably distinguishable such as by being of different sizes or having distinguishable labels. Such a use of differently sized microbeads or microbeads labelled such as with fluorophores allows the identification and/or separation of different beads by flow cytometry.

According to a general method of practicing the invention, HLA antigen coated microbeads are incubated with serum to be tested for 30 minutes at 20°–25° C. at a suitable dilution which may readily be determined by those of skill in the art but preferably ranges from neat to a dilution of 1:10. The microbeads are then washed with wash buffer comprising PBS with 0.1% polysorbate 20 (TWEEN® 20 ) three times and are incubated with Goat anti-Human IgG antibodies conjugated with PE Phycocrythrin or FITC (fluorescine isothiocyanate) fluorescent labels and incubated for 30 minutes. The microbeads are then washed two times with wash buffer and analyzed on a flow cytometer. Sera which contains anti-HLA antibodies will show a fluorescent channel shift compared to negative sera. Signal thresholds can be established by testing both positive and negative control samples. Using such a cut-off, anti-HLA positive serum will be assigned by a higher fluorescent channel shift than the threshold while negative anti-HLA sera will be assigned by a lower fluorescent channel shift than the threshold. The reactivity of all of the bound antigens may be confirmed by the serological defined human alloantisera.

According to one aspect of the invention, a mixture of microbeads coated with a panel of purified HLA antigen selected to simulate the frequency of those antigens in a normal population may be used to determine the percentage of PRA. The percentage of PRA is represented by the percentage of the microbeads which are positive.

Other aspects and advantages of the present invention will be understood upon consideration of the following illustrative examples.

EXAMPLE 1

According to this example, Class I HLA antigen preparations were purified from Epstein Barr virus transformed lymphocyte cell lines according to the methods of Henderson et al., *Virology* 76: 152–163 (1977). Thirty of the Class I HLA antigen preparations were then selected to simulate the distribution of HLA in a normal population as set out in Table 1 and were coated by passive absorption onto 3 μm latex beads obtained from Spherotech according to the method of Cantarero et al., *Anal. Biochem.*, 105: 373–382 (1980).

TABLE 1

| Bead No. | HLA CLASS I Antigen Typing | |
| --- | --- | --- |
| 1 | A11 | B27, 48 |
| 2 | M2, 29 | B39, 56 |
| 3 | A1, 29 | B8, 45 |
| 4 | A2, 24 | B7, 55 |
| 5 | A2, 25 | B18, 64 |
| 6 | A26, 24 | B52, 62 |
| 7 | A31, 68 | B53 |
| 8 | A2, 11 | B13, 62 |
| 9 | A23, 33 | B45, 63 |
| 10 | A23, 34 | B44 |
| 11 | A11, 23 | B49, 52 |
| 12 | A11, 24 | B59, 60 |
| 13 | A24, 33 | B44, 51 |
| 14 | A23, 26 | B41, 72 |
| 15 | A3, 32 | B50, 56 |
| 16 | A2, 24 | B54, 67 |
| 17 | A2 | B52, 73 |
| 18 | A26, 66 | B38, 75 |
| 19 | A11, 33 | B51, 54 |
| 20 | A30 | B13, 72 |
| 21 | A30, 36 | B35, 71 |
| 22 | A69 | B35, 61 |
| 23 | A1, 32 | B60, 64 |
| 24 | A2 | B7, 46 |
| 25 | A30 | B42 |
| 26 | A2 | B8, 58 |
| 27 | A2, 3 | B58, 65 |
| 28 | A1, 36 | B37, 57 |
| 29 | A3, 68 | B7, 65 |
| 30 | A33, 36 | B53, 61 |

The reactivity of the HLA antigen on each bead was confirmed by a panel of serologically defined HLA inonoclonal antibodies or by human allosera using a flow cytometry test. Each bead reacted specifically to the HLA monoclonal antibodies or allosera with the same HLA specificity.

The sensitivity of the beads was tested by mixing two beads with different typing at different percentages. A minimum of 2 to 3% of one kind of bead was found to be sufficient to detect the antigen.

EXAMPLE 2

According to this example, the sensitivity of the microbeads useful with the invention was tested by carrying out a serial dilution of selected PRA sera. The results presented in Table 2 below show that most PRA sera decrease the percentage of reactivity at a 1:10 dilution measured by a cytotoxicity test while they did not decrease the percentage of reactivity at a 1:40 dilution by use of the microbeads in a flow cytometry device according to the invention.

TABLE 2

| Sera ID | Dilution | Percentage Cytotoxicity | Flow Cytometry |
|---|---|---|---|
| N21 | 1 | 40 | |
| | 1:10 | 10 | 41 |
| | 1:20 | 0 | 30 |
| | 1:40 | 0 | 41 |
| | 1:50 | 0 | 18 |
| | 1:160 | 0 | 16 |
| A2 | 1 | 30 | |
| | 1:20 | 0 | 25 |
| | 1:40 | 0 | 26 |
| | 1:80 | 0 | 8 |
| S193 | 1 | 25 | |
| | 1:10 | 31 | 28 |
| | 1:20 | 17 | 100 |
| | 1:40 | 10 | 100 |
| | 1:80 | 0 | 100 |
| S176 | 1 | 54 | |
| | 1:10 | 24 | 40 |
| | 1:20 | 28 | 41 |
| | 1:40 | 10 | 40 |
| | 1:50 | 0 | 40 |
| S199 | 1 | 100 | |
| | 1:10 | 10 | 97 |
| | 1:20 | 3 | 97 |
| | 1:40 | 10 | 97 |
| | 1:50 | 3 | 99 |
| B73 | 1 | 65 | |
| | 1:10 | 27 | 54 |
| | 1:20 | 3 | 40 |
| | 1:40 | 3 | 43 |
| | 1:50 | 0 | 25 |

EXAMPLE 3

According to this example, an assay to detect panel reactive antibodies was carried out by mixing 10 μl of a mixture of the 30 different types of beads produced according to Example 1 with 100 μl (1:10 diluted) serum to be tested and incubating for 30 minutes at 20°–25° C. with gentle rotating. The beads were then washed three times with 1 mL of wash buffer. The beads were then incubated with 100 μl of 1:100 diluted Goat anti-human IgG-PE obtained from Jackson InnumoResearch for 30 minutes. The beads were then washed twice and 1 mL of wash buffer and read on a flow cytometer (B. D. FacStar Plus). The percentage of PRA is represented by the percentage of microbeads which are positively labelled.

According to this example, 61 sera samples including 22 negative and 39 PRA patients who had panel reactive antibody activities developed by earlier transplantation or transfusion were tested with the results shown in FIG. 1 which shows the correlation of the flow cytometry results with those where the same samples were tested by complement-dependent lymphocytotoxicity. The correlation coefficient R is 0.94 for the 61 data points indicating a high degree of correlation between results obtained by flow cytometry and those obtained by a cytotoxicity test.

EXAMPLE 4

According to this example, 30 Class II HLA antigen preparations as set out in Table 3 were purified from Epstein Barr virus transformed lymphocyte cell lines according to the methods of Henderson et al., *Virology* 76: 152–163 (1977). The antigen preparations may then be coated by passive absorption onto 5 μm latex beads obtained from Spherotech according to the method of Cantarero et al., *Anal. Biochem.*, 105: 373–382 (1980). From this collection of Class II HLA preparations, from 15 to 30 beads may selected to simulate the distribution of the 22 Class II HLA antigens in a normal population.

TABLE 3

| Beads No. | HLA Class II Antigen Typing | | |
|---|---|---|---|
| 1 | DR15, 9 | 53, 51 | DQ5, 9 |
| 2 | DR4, 15 | 53, 51 | DQ6, 7 |
| 3 | DR16, 4 | 53, 51 | DQ4, 5 |
| 4 | DR8, 14 | 52 | DQ4, 5 |
| 5 | DR4, 7 | 53 | DQ2, 8 |
| 6 | DR15, 18 | 51, 52 | DQ6, 4 |
| 7 | DR11, 12 | 52 | DQ5, 7 |
| 8 | DR103, 17 | 52 | DQ5, 2 |
| 9 | DR1, 13 | 52 | DQ5, 6 |
| 10 | DR9, 10 | 53 | DQ5, 9 |
| 11 | DR15, 12 | 51, 52 | DQ5, 7 |
| 12 | DR16, 14 | 51, 52 | DQ5 |
| 13 | DR13, 8 | 52 | DQ5, 6 |
| 14 | DR11, 13 | 52 | DQ5, 6 |
| 15 | DR17, 7 | 52, 53 | DQ2, 9 |
| 16 | DR15, 8 | 51 | DQ6, 8 |
| 17 | DR15, 4 | 51, 53 | DQ2, 6 |
| 18 | DR15, 17 | 51, 52 | DQ6, 2 |
| 19 | DR15, 7 | 51, 53 | DQ6, 2 |
| 20 | DR1, 7 | 53 | DQ2, 5 |
| 21 | DR15, 11 | 52 | DQ5, 6 |
| 22 | DR7, 13 | 52, 53 | DQ6, 9 |
| 23 | DR15, 13 | 51, 52 | DQ6, 2 |
| 24 | DR9, 14 | 52, 53 | DQ5, 9 |
| 25 | DR8, 9 | 53 | DQ2, 7 |
| 26 | DR17, 14 | 52 | DQ2, 5 |
| 27 | DR1, 11 | 52 | DQ5, 6 |
| 28 | DR17, 4 | 52, 53 | DQ2 |
| 29 | DR11, 4 | 52, 53 | DQ7, 8 |
| 30 | DR1, 14 | 52 | DQ5 |

EXAMPLE 5

Figure 2A:
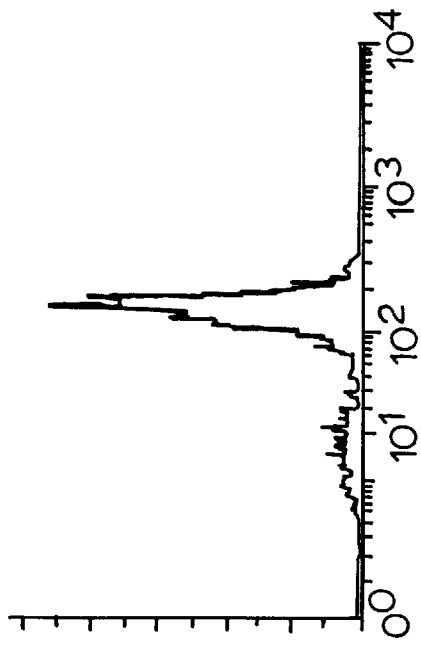
FIGS. 2a–2d depict the reaction of the mixture of Class I and Class II beads and their reaction to anti-HLA Class I antibodies (FIGS. 2a and 2b) or anti-HLA Class II antibodies (FIGS. 2c and 2d).
Figure 2B:
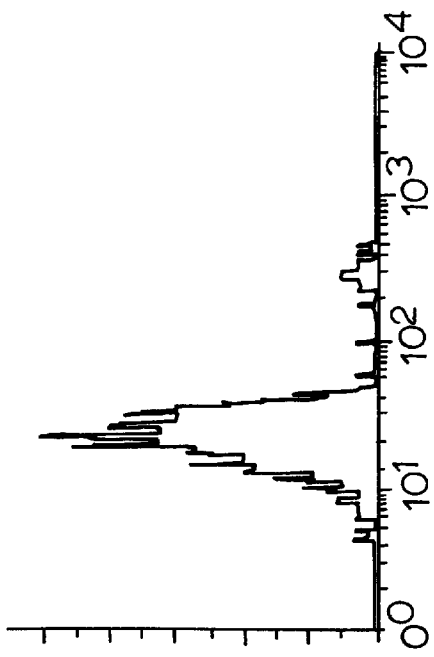
Figure 2C:
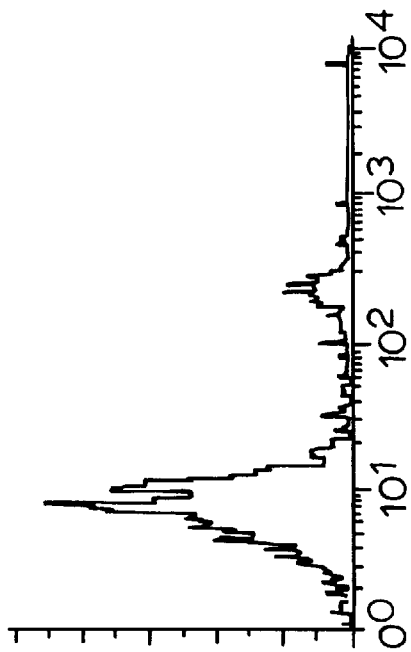
Figure 2D:
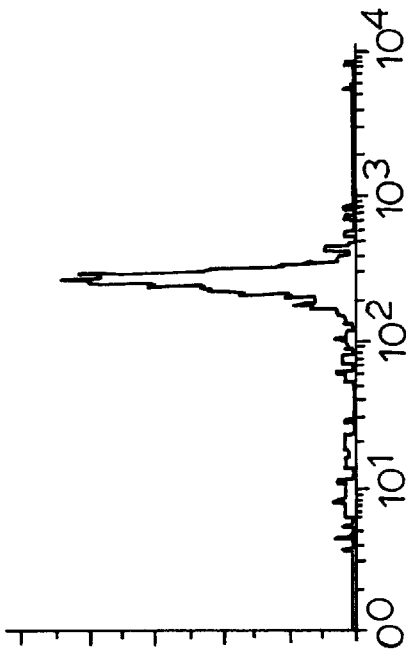

According to this example, 3 μm latex beads presenting HLA Class I antigens produced according to the methods of example 1 and 5 μm latex beads presenting HLA Class II antigens produced according to the methods of example 4 were mixed to perform an assay to detect the presence of antibodies specific to HLA Class I and Class II antigens. Because the beads presenting HLA Class II antigens are different in size from the HLA Class I beads, the two different sized beads can be electronically distinguished according to their sizes when analyzed on a flow cytometer as illustrated in FIGS. 2a–2d. FIG. 2a–d depict the reaction of the mixture of Class I and Class II beads and their reaction to anti-HLA Class I antibodies (FIGS. 2a and 2b) or anti-HLA Class II antibodies (FIGS. 2c and 2d). When the Class I beads are selected by gating around the 3 μm size, the beads react to the anti-Class I antibody as illustrated in FIG. 2a. When the Class II beads are selected by gating around the 5 μm size, there is no reaction to the anti-Class I antibody as illustrated in FIG. 2b. The reaction pattern of the mixed beads to the anti-class II antibody is the reverse. When Class I beads are selected by gating around 3 μm in size, the beads do not react to the anti-Class II antibody as illustrated in FIG. 2c. When Class II antibodies are selected by gating around 5 μm in size, the Class II antigen beads react to the anti-Class II antibody as illustrated in FIG. 2d.

Numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

What is claimed is:

1. A method for determining the percentage of panel reactive antibodies in serum of a subject against HLA antigens, said method comprising:

providing a collection of microbeads of different subtypes, wherein each subtype is coated with different purified HLA antigens, and the microbeads of at least one subtype each present HLA antigens derived from a cell population presenting the same HLA antigens;

adding said serum from said subject to said collection of microbeads;

incubating said serum and microbeads for sufficient time for anti-HLA antibodies in said serum to bind to said HLA antigens;

removing said serum components which do not specifically bind with said HLA antigens presented on said microbeads;

incubating said microbeads with at least one labeled ligand capable of specifically binding with said anti-HLA antibodies bound to said HLA antigens;

removing labeled ligand which is not bound to said anti-HLA antibodies; and detecting the presence of labeled ligand bound to said anti-HLA antibodies by flow cytometry to determine the presence or absence of panel reactive antibodies:

and, determining the percentage of panel reactive antibodies.

2. The method of claim 1 wherein the microbeads of each subtype present HLA antigens derived from a single lymphocyte cell line.

3. The method of claim 1 wherein the HLA antigens are Class I HLA antigens.

4. The method of claim 1 wherein the collection of microbeads is selected such that the HLA antigens presented thereon simulate distribution of Class I HLA antigens in a normal human population.

5. The method of claim 4 wherein said multibead collection comprises 54 different Class I HLA antigens.

6. The method of claim 5 wherein said multibead collection comprises 54 different Class I HLA antigens purified from 30 different cells.

7. The method of claim 1 wherein the HLA antigens are Class II HLA antigens.

8. The method of claim 7 wherein said collection comprises 22 different Class II HLA antigens.

9. The method of claim 1 wherein the microbeads are latex.

10. The method of claim 1 wherein microbeads of at least one HLA subtype differ from microbeads of at least one other HLA subtype by being selected to have different diameters.

11. The method of claim 1 wherein microbeads of at least one HLA subtype differ from microbeads of at least one other HLA subtype by being labeled with different labels.

12. The method of claim 11 wherein the labels are fluorescent labels.

13. The method of claim 1 wherein the microbeads range in diameter from about 2 $\mu$m to about 15 $\mu$m.

14. The method of claim 12 wherein the microbeads are approximately 3 $\mu$m in diameter.

15. The method of claim 1 wherein said microbeads comprise a mixture of 3 $\mu$m microbeads presenting Class I HLA antigens and 5 $\mu$m microbeads presenting Class II HLA antigens.

* * * * *